United States Patent [19]
Danysz et al.

[11] Patent Number: 5,776,935
[45] Date of Patent: Jul. 7, 1998

[54] PYRIDO-PHTALAZIN DIONES AND THEIR USE AGAINST NEUROLOGICAL DISORDERS ASSOCIATED WITH EXCITOTOXICITY AND MALFUNCTIONING OF GLUTAMATERGIC NEUROTRANSMISSION

[75] Inventors: Wojciech Danysz, Nidderau; Markus Gold, Nauheim, both of Germany; Ivars Kalvinsh, Salaspils, Latvia; Christopher Graham Raphael Parsons, Praunheim, Germany; Irene Piskunova; Eugene Rozhkov, both of Riga, Latvia

[73] Assignee: Merz & Co. GmbH & Co., Frankfurt, Germany

[21] Appl. No.: 686,346

[22] Filed: Jul. 25, 1996

[51] Int. Cl.$^6$ .................. A61K 31/50; C07D 471/04
[52] U.S. Cl. ............................. 514/248; 544/234
[58] Field of Search ............................. 514/248; 544/234

[56] References Cited

U.S. PATENT DOCUMENTS

| | | | |
|---|---|---|---|
| 5,597,922 | 1/1997 | Cai et al. | 544/234 |
| 5,599,814 | 2/1997 | Bare et al. | 544/234 |

FOREIGN PATENT DOCUMENTS

0 516 297  6/1992  European Pat. Off. .

OTHER PUBLICATIONS

O. A. Andreassen et al., British Jour. of Pharm. 119 751–757 (1996) "Inhibition by Memantine of the Development of persistent oral dyskinesias induced by long–term haloperidol treatment of rats".

S. Angus et al., Jour. of Clinical Psychopharmacology 17 88–91 (1997) "A Controlled Trial of Amantadine Hydrochloride and Neuroleptics in the Treatment of Tardive Dyskinesia".

Backhauss, C., Karkoutly, C., Welsch, M., & Krieglstein, J., Jour. of Pharmacological Methods 27 27–32 (1992) "A Mouse Model of Focal Cerebral Ischemia for Screenig Neuroprotective Drug Effects".

Backhauss, C. & Krieglstein, J., Eur. Jour. of Pharmacology 215 265–269 (1992) "Extract of kava (Piper methysticum) and its methysticin constituents protect brain tissue against ischemic damage in rodents."

C.A. Barness et al., Eur. Jour. of Neuroscience 8 565–571 (1996) "Effects of the Uncompetitive NMDA Receptor Antagonists Memantine on Hippocampal Long–Term Potentiation, Short–term Exploratory Modulation and Spatial Memory in Awake, Freely Moving Rats".

M.F. Beal et al., TINS 16 125–131 (1993) "Do defects in mitochondrial energy metabolism underlie the pathology of neurodegenerative diseases?".

G. Bensimon et al., New Eng. Jour. of Medicine 330 585–591 (1994) "A Controlled Trial of Riluzole in Amyotrophic Lateral Sclerosis".

F. Block et al., Neuroscience Letters 208 41–44 (1996) "Memantine reduces functional and morphological consequences induced by global ischemia in rats".

M.I. Botez et al., Jour. of Neurology, Neurosurgery, & Psychiatry 61 259–264 (1996) "Amantadine hydrochloride treatment in heredodegenerative ataxias: a double blind study".

Bristow, L.J., Flatman, K.L., Hutson, P.H., Kulagowski, J.J., Leeson, P.D., Young, L. & Tricklebank, M.D., Jour. of Pharm. & Experimental Therapeutics 277 578–585 (1996) "The Atypical Neuroleptic Profile of the Glycine/N-Methyl-D-Aspartate Receptor Antagonist, L-701,324 in Rodents".

Bristow, L.J., Landon, L., Saywell, K.L., & Tricklebank, M.D., Psychopharmacology 118 230–232 (1995) "The glycine/NMDA receptor antagonists, L-701,324 reverse isolation–induced deficits in prepulse inhibition in the rat".

R.F. Butterworth, Hepatology 25 1032–1034 (1997) "Hepatic Encephalopathy and Brain Edema in Acute Hepatic Failure: Does Glutamate Play a Role?".

S. M. Carlton et al., Neuroscience Letters 198 115–118 (1995) "Treatment with the NMDA antagonist memantine attenuates nociceptive responses to mechanical stimulation in neuropathic rats".

S. R. Chaplan et al., Jour. of Pharm. & Experimental Therapeutics 280 829–838 (1997) "Efficacy of Spinal NMDA Receptor Antagonism in Formalin Hyperalgesia and Nerve Injury Evoked Allodynia in the Rat".

E. Chojnacka–Wojcik et al., Pol. J. Pharmacol. Pharm. 35 511–515 (1983) "The Influence of Memantine on the Anticonvulsant Effects of the Antiepileptic Drugs".

R. Corbett et al., Drug Development Research 24 201–205 (1991) "Effects of HA–966 on Conflict, Social Interaction, and Plus Maze Behaviors".

(List continued on next page.)

*Primary Examiner*—Emily Bernhardt
*Attorney, Agent, or Firm*—The Firm of Gordon W. Hueschen

[57] ABSTRACT

Pyridyl-phtalazin diones having the following formula:

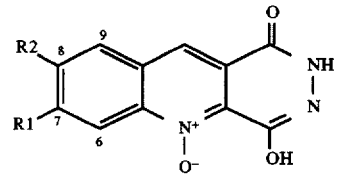

wherein R1 and R2 are selected from the group consisting of hydrogen, halogen, and methoxy or wherein R1 and R2 together form methylenedioxy, and pharmaceutically-acceptable salts thereof, and pharmaceutical compositions containing an effective glycine$_B$ antagonistic amount thereof, are useful in combatting neurological disorders associated with excitotoxicity and malfunctioning of glutamatergic neurotransmission in a living animal, including a human, in need thereof.

12 Claims, No Drawings

OTHER PUBLICATIONS

S.J. Czuczwar et al., Metabolic Brain Disease 11 143–152 (1996) "Interactions of Excitatory Amino Acid Antagonists with Conventional Antiepileptic Drugs".

Danysz, W., Essmann, U., Bresink, I., & Wilke, R., Pharm. Biochemistry & Behavior 48 111–118 (1994) "Glutamate Antagonists Have Different Effects on Spontaneous Locomotor Activity in Rats".

Danysz, W. Gossel, M., Zajaczkowski, W., Dill, D., & Quack, G., J. Neural Transm. 7 155–166 (1994) "Are NMDA antagonistic properties relevant for antiparkinsonian–like activity in rats?—Case of amantadine and memantine".

Danysz, W., Parsons, C.G., Kornhuber, J., Schmidt, W.J., & Quack, G., Neuroscience & Biobehavioral Reviews 21 455–468 (1997) "Aminoadamantanes as NMDA Receptor Antagonists and Antiparkinsonian Agents—Preclinical Studies".

A.H. Dickenson et al., Neuroscience Letters 121 263–266 (1991) "Antagonism at the glycine site on the NMDA receptor reduces spinal nociception in the rat".

R.W. Dunn et al., Eur. Jour. of Pharmacology 214 207–214 (1992) "Stereoselective R–(+) enantiomer of HA–966 displays anxiolytic effects in rodents".

Eisenberg, E., LaCross, S., & Strassman, A.M., Neuroscience Letters 187 17–20 (1995) "The clinically tested N–methyl–D–aspartate receptor antagonist memantine blocks and reverses thermal hyperalgesia in a rat model of painful mononeuropathy".

Eisenberg, E., LaCross, S., & Strassman, A.M., Eur. Jour. of Pharmacology 255 123–129 (1994) "The effects of the clinically tested NMDA receptor antagonist memantine on carrageenan–induced thermal hyperalgesia in rats".

Eisenberg, E., Vos, B.P., & Strassman, A.M., Pain 54 301–307 (1993) "The NMDA antagonist Memantine blocks pain behavior in a rat model of formalin–induced facial pain".

C.P. Faiman et al., Jour. of Pharm. & Experimental Therapeutics 270 528–533 (1994) "Differential Effects of Compounds that Act at Strychnine–Insensitive Glycine Receptors in a Punishment Procedure".

S. Farkas et al., Pharm. Research Comm. 20 141 (1988) "Electromyographic Measurement of the Flexor Reflex in Cats for Testing Centrally Acting Muscle Relaxant Drugs".

H.H. Frey et al., Neuropharmacology 30 651–656 (1991) "Effect of Psychotropic Agents on a Model of Absence Epilepsy in Rats".

R. Gill et al., Jour. of Cerebral Blood Flow & Metabolism 15 197–204 (1995) "The Neuroprotective Effect of the Glycine Site Antagonist 3R–(+)–cis–4–Methyl–HA966 (L–687414) in a Rat Model of Focal Ischaemia".

L.E. Goldstein et al., Jour. of Neuroscience 14 4937–4950 (1994) "The NMDA Glycine Site Antagonist (+)–HA–966 Selectively Regulates Conditioned Stress–Induced Metabolic Activation of the Mesoprefrontal Cortical Dopamine but Not Serotonin Systems: A Behavioral, Neuroendocrine, and Neurochemical Study in the Rat".

Gortelmeyer, R., & Erbler, H., Drug Research 42 904–913 (1992) "Memantine in the Treatment of Mild to Moderate Dementia Syndrome".

Gortelmeyer, R., Pantev, M., Parsons, C.G., & Quack, G...Spektrum der Neurorehabilitation 1–10 (1993) "Die Behandlung des dementiellen Syndroms mit Akatinol Memantine, einem Modulator des glutamatergen Systems".

Hesselink, pp. 1–4 (1997) Microdialysis Studies with MERZ 2/570, 2/571 and 2/576.

S. M. Holter et al., Eur. Jour. of Pharmacology 314 R1–R2 (1996) "Evidence for alcohol anti–craving properties of memantine".

J.H. Kehne et al., Eur. Jour. of Pharmacology 284 109–118 (1995) "MDL 100,458 and MDL 102,288: two potent and selective glycine receptor antagonists with different functional profiles".

K. Kieburtz et al., Movement Disorders 11 273–277 (1996) "A Controlled Trial of Remacemide Hydrochloride in Huntington's Disease".

M.D. Kopelman, Brit. Jour. of Psychiatry 166 154–173 (1995) "The Korsakoff Syndrome".

Lutfy, K., Cai, S.X., Woodward, R.M., Weber, E., Pain 70 31–40 (1997) "Antinociceptive effects of NMDA and non-–NMDA receptor antagonists in the tail flick test in mice".

Lutfy, K., Cai, S.X., Woodward, R.M., Weber, E., Brain Research 731 171–181 (1996) "Inhibition of morphine tolerance by NMDA receptor antagonists in the formalin test".

Lufty, K., Shen, K., Kwon, I., Cai, S.X., Woodward, R.M., Keana, J.F.W., & Weber, E., Eur. Jour. of Pharmacology 273 187–189 (1995) "Blockade of morphine tolerance by ACEA–1328, a novel NMDA receptor/glycine site antagonist".

Lufty, K., Cai, S.X., Woodward, R.M., Weber, E., Eur. Jour. of Pharmacology 252 261–266 (1994) "Inhibition of clonic seizure–like excitatory effects induced by intrathecal morphine using two NMDA receptor antagonists: MK–801 and ACEA–1011".

M.B. Max et al., Clinical Neuropharmacology 18 360–368 (1995) "Intravenous Infusion of the NMDA Antagonist, Ketamine, in Chronic Posttraumatic Pain with Allodynia: A Double–Blind Comparison to Alfentanil and Placebo".

B.S. Meldrum et al., Naunyn–Schmiedeberg's Arch. Pharmacol 332 93–97 (1986) "Anticonvulsant action of 1,3–dimethyl–5–aminoadamantane".

M.J. Millan et al., Neuroscience Letters 178 139–143 (1994) "Chemically–diverse ligands at the glycine B site coupled to N–methyl–D–aspartate (NMDA) receptors selectively block the late phase of formalin–induced pain in mice".

M. Misztal et al., Eur. Jour. of Pharmacology 296 1–8 (1996) "Learning deficits induced by chronic intraventricular infusion of quinolinic acid–protection by MK–801 and memantine".

B.A. Morrow et al., Brain Research 673 165–169 (1995) "R–(+)–HA–966, an antagonist for the glycine/NMDA receptor, prevents locomotor sensitization to repeated cocaine exposures".

E. Moryl et al., Pharmacology & Technology 72 394–397 (1993) "Potential Antidepressive Properties of Amantadine, Memantine and Bifemelan".

B. Muhlberg et al., Naunyn–Schmiedeberg's Arch. Pharmacol. 280 113–116 (1973) "The Depression of Monosynaptically Excited a–Motoneurons during Vibration Reflex by Dimethylaminoadamantan (DMAA)".

Muller, W.E., Mutschler, E., Riederer, P., Pharmacopsychiatry 287 113–124 (1995) "Noncompetitive NMDA Receptor Antagonists with Fast Open–Channel Blocking Kinetics and Strong Voltage–Dependency as Potential Therapeutic Agents for Alzheimer's Dementia".

Muller, W.E., Ushijima, H., Schroder, H.C., Forrest, J.M.S., Schatton, W.F.H., Rytik, P.G., Heffner–Lauc, M., Eur. Jour. of Pharmacology 246 261–267 (1993) "Cytoprotective effect of NMDA receptor antagonists on prion protein (Prion$^{Sc}$)–induced toxicity in rat cortical cell cultures".

V. Neugebauer et al., NeuroReport 4 1259–1262 (1993) "The clinically available NMDA receptor antagonist memantine is antinociceptive on rat spinal neurones".

J. Noth, Jour. of Neurology 238 131–139 (1991) "Trends in the pathophysiology and pharmacotherapy of spasticity".

Parsons, C.G., Collingridge, G.L., Potier, B., Frankiewicz, T., Zajaczkowski, W., Misztal, M., and Danysz, W., Society for Neuroscience (1995) "Uncompetitive NMDA Receptor Antagonists (MK–801 and Memantine) impair or enhance learning depending on dose and experimental design—comparison with effects on LTP in vitro".

Parsons, C.G., Quack, G., Bresink, I., Baran, L., Przegalinski, E., Kostowski, W., Krzascik, P., Hartmann, S. and Danysz, W., Neuropharmacology 34 1239–1258 (1995) "Comparison of the Potency, Kinetics and Voltage–dependency of a Series of Uncompetitive NMDA Receptor Antagonists in vitro with Anticonvulsive and Motor Impairment Activity in Vivo".

M. Pantev, et al., Zeitschrift fur Geronto–psychologie & –psychiatrie 6 103–117 (1993) "Clinical and behavioural evaluation in long–term care patients with mild to moderate dementia under Memantine treatment".

Popik, P., Danysz, W., Jour. of Pharmacology and Experimental Therapeutics 280 854–865 (1997) "Inhibition of Reinforcing Effects of Morphine and Motivational Aspects of Naloxone–Precipitated Opioid Withdrawal by N–Methyl–D–Aspartate Receptor Antagonists. Memantine".

Popik, P., Layer, R.T., Fossom, L.H., Benveniste, M., Geter–Douglass, B., Witkin, J.M., Skolnick, P., Jour. of Pharmacology and Experimental Therapeutics 275 753–760 (1995) "NMDA Antagonist Properties of the Putative Antiaddictive Drug, Ibogaine".

Popik, P., Skolnick, P., Pharm. Biochemistry and Behavior 53 791–797 (1996) "The NMDA Antagonist Memantine Blocks the Expression and Maintenance of Morphine Dependence".

A. Plaitakis et al., Pharmacology and Pathophysiology 5 437–456 (1996) "Glutamate Antagonists in Amyotrophic Lateral Sclerosis".

T. Priestley et al., Brain Research 531 183–188 (1990) "The effect of NMDA receptor glycine site antagonists on hypoxia–induced neurodegeneration of rat cortical cell cultures".

E. Przegalinski et al., Pharm. Biochemistry and Behavior 54 73–77 (1996) "Anticonflict Effects of a Competitive NMDA Receptor Antagonist and a Partial Agonist at Strychnine–Insensitive Glycine Receptors".

G. Quack et al., Jour. Neural Transm 46 97–105 (1995) "Microdialysis studies with amantadine and memantine on pharmacokinetics and effects on dopamine turnover".

A. Richter et al., Neuroscience Letters 133 57–60 (1991) "Antidystonic effects of the NMDA receptor antagonists memantine, MK–801 and CGP 37849 in a mutant hamster model of paroxysmal dystonia".

Schmidt, W.J., Zadow, B., Kretschmer, B.D., & Hauber, W., Amino Acids 1 225–237 (1991) "Anticataleptic potencies of glutamate–antagonists".

Schmidtd, W.J., Bubser, M., & Hauber, W., J. Neural Transm 38 65–89 (1992) "Behavioural pharmacology of glutamate in the basal ganglia".

J.B. Schulz et al., Neuroscience 71 1043–1048 (1996) "Neuroprotective Strategies for Treatment of Lesions Produced by Mitrochondrial Toxins: Implications for Neurodegenerative Diseases".

M. Schwarz et al., Neuroscience Letters 143 105–109 (1992) "N–Methyl–D–Aspartate (NMDA)–mediated muscle relaxant action of memantine in rats".

M.S. el Nasr et al., Eur. Jour. of Pharmacology 185 19–24 (1990) "Neuroprotective effect of memantine demonstrated in vivo and in vitro".

G. Skuza et al., J. Neural Transm 98 57–67 (1994) "Memantine, amantadine, and L–deprenyl potentiate the action of L–DOPA in monoamine–depleted rats".

Sontag, K.H., & Wand, P., Drug Research 23 1737–1739 (1973) "Decrease of Muscle Rigidity by Dimethylaminoadamantan (DMMA) in Intercollicularly Decerebrated Cats".

Sontag, K.H., Wand, P., Cremer, H., Mulhberg, B., Naunyn Schmiedeberg's Arch. Pharmacol. 286 315–318 (1974) "The Reduction of Excitability of the Y–Loop by 1,3–Dimethyl–5–aminoadamantane (DMAA)".

Spanagel, R., Eilbacher, B., Wilke, R., Eur. Jour. of Pharmacology 262 21–26 (1994) "Memantine–induced dopamine release in the prefrontal cortex and striatum of the rat—a pharmacokinetic microdialysis study".

Spanagel, R., Zieglgansberger, W., TiPS 18 54–59 (1997) "Anti–craving compounds for ethanol: new pharamcological tools to study addictive processes".

S.M. Toggas et al., Brain Research 706 303–307 (1996) "Prevention of HIV–1 gp120–induced neuronal damage in the central nervous system of transgenic mice by the NMDA receptor antagonist memantine".

Trullas, R., Folio, T., Young, A., Miller, R., Boje, K., & Skolnick, P., Eur. Jour. of Pharmacology 203 379–385 (1991) "1–Aminocyclopropanecarboxylates exhibit antidepressant and anxiolytic actions in animal models".

Trullas, R., Jackson, B., & Skolnick, P., Pharmacology Biochemistry & Behavior 34 313–316 (1989) "Anxiolytic Properties of 1–Aminocyclopropanecarboxylic Acid, a Ligand at Strychnine–Insensitive Glycine Receptors".

Trullas, R., Skolnick, P., Eur. Jour. of Pharmacology 185 1–10 (1990) "Functional antagonists at the NMDA receptor complex exhibit antidepressant actions".

E. Tsuchida et al., Jour. of Neurotrauma 12 279–288 (1995) "The Effect of the Glycine Site–Specific N–Methyl–D–Aspartate Antagonist ACEA1021 on Ischemic Brain Damage Caused by Acute Subdural Hematoma in the Rat".

R.J. Uitti et al., Neurology 46 1551–1556 (1996) "Amantadine treatment is an independent predictor of improved survival in Parkinson's disease".

E. Urbanska et al., Neuropharmacology 31 1021–1026 (1992) "Antiparkinsonian Drugs Memantine and Trihexyphenidyl Potentiate the Anticonvulsant Activity of Valproate Against Maximal Electroshock–Induced Seizures".

A.L. Vaccarino et al., Brain Research 615 331–334 (1993) "NMDA receptor antagonists, MK–801 and ACEA–1011, prevent the development of tonic pain following subcutaneous formalin".

B.A.P.M. Vogels et al., Hepatology 25 820–827 (1997) "Memantine, a Noncompetitive NMDA Receptor Antagonist Improves Hyperammonemia–Induced Encephalopathy and Acute Hepatic Encephalopathy in Rats".

E. Wallstrom et al., Jour. of Neurological Sciences 137 89–96 (1996) "Memantine abrogates neurological deficits, but not CNS inflammation, in Lewis in rat experimental autoimmune encephalomyelitis".

P. Wand et al., Drug Research 27 8–11 (1977) "Effects of 1,3-Dimethyl-5-aminoadamantane Hydrochloride (DMAA, on the Stretch–induced Reflex Tension of Flexor Muscles and the Excitability of the y–Loop in Decerebrate and Spinal Cats".

D.S. Warner et al., Jour. of Cerebral Blood Flod and Metabolism 15 188–196 (1995) "In Vivo Models of Cerebral Ischemia: Effects of Parenterally Administered NMDA Receptor Glycine Site Antagonists".

G.L. Wenk, Final Report—Jul. 2, 1996, "Investigation of the Neuroprotective Properties of Compound 2/570, Administered by Minipump, in Rats Given Injections of NMDA into the Basal Forebrain".

G.L. Wenk, Final Report—Mar. 27, 1997 "Investigation of the Neuroprotective Properties of Compounds 2/571 and 2/576, Administered Acutely, in Rats Given Acute Injections in NMDA into the NBM".

Wenk, G.L., Danysz, w., Mobley, S.L., Eur. Jour. of Pharmacology 293 267–270 (1995) "MK–801, memantine and amantadine show neuroprotective activity in the nucleus basalis magnocellularis".

Wenk, G.L., Danysz, W., Mobley, S.L., Brain Research 655 7–11 (1994) "Investigations of neurotoxicity and neuroprotection within the nucleus basalis of the rat".

Wenk, G.L., Danysz, W., Mobley, S.L., NeuroReport 7 1453–1456 (1996) "The effects of mitochondrial failure upon cholinergic toxicity in the nucleus basalis".

W. Zajaczkowski et al., Eur. Jour. of Pharmacology 296 239–246 (1996) "Infusion of (+)–MK–801 and memantine—contrasting effects of radial maze learning rats with entorhinal cortex lesion".

Choi, *Neuron* 1, pp. 623–634 (1988).

Koh et al, *Brain Research* 533, pp. 315–320 (1990).

Trujillo et al, *Science* 251, pp. 85–87 (1991).

PYRIDO-PHTALAZIN DIONES AND THEIR USE AGAINST NEUROLOGICAL DISORDERS ASSOCIATED WITH EXCITOTOXICITY AND MALFUNCTIONING OF GLUTAMATERGIC NEUROTRANSMISSION

FIELD OF INVENTION

New chemical compounds which are pyrido-phtalazin diones, pharmaceutical compositions containing the same, and their use against neurological disorders associated with excitotoxicity and malfunctioning of glutamatergic neurotransmission.

BACKGROUND OF THE INVENTION AND PRIOR ART

Glutamate is probably the major excitatory transmitter in the central nervous system but is also likely to be involved in many pathological and excitotoxic processes. As such there is a great deal of interest in the development of glutamate antagonists for therapeutic use (see Danysz et al., 1995 for review). Glutamate activates three major types of ionotropic receptor, namely α-amino-3-hydroxy-5-methyl-4-isoxazolepropionic acid (AMPA), kainate and N-methyl-D-aspartate (NMDA) and several types of metabotropic receptors. Antagonism of NMDA receptors potentially has a wide range of therapeutic applications. Functional inhibition of NMDA receptors can be achieved through actions at different recognition sites such as the primary transmitter site, strychnine-insensitive glycine site (glycine$_B$), polyamine site, and phencyclidine site located inside the cation channel.

Receptor desensitisation may represent a physiological process serving as an endogenous control mechanism to prevent long term neurotoxic activation of glutamate receptors but allow their transient physiological activation. In the case of the NMDA receptor, the coagonist glycine is an endogenous ligand inhibiting such desensitisation via activation of the glycine$_B$ site. Interestingly, ischaemia increases not only the concentration of extracellular glutamate but also that of glycine and, although this latter effect is less pronounced, it actually persists for much longer. Hence, some full glycine$_B$ antagonists could restore normal synaptic transmission under such conditions by increasing NMDA receptor desensitisation to its physiological level. Indeed, it has been suggested on the basis of central administration in laboratory animals that glycine$_B$ antagonists may offer a better therapeutic window than agents acting at other recognition sites of NMDA receptor complex. Unfortunately, poor pharmacokinetic properties of most glycine$_B$ antagonists have, until very recently, excluded clear verification of this suggestion after systemic administration. However, some glycine$_B$ antagonists have been reported to have very good therapeutic indices following systemic administration in models of hyperalgesia and as anxiolytics.

THE PRESENT INVENTION

We have now developed a series of tricyclic "pyridophtalazin diones". Compounds of class I are structurally related to patented glycine$_B$ antagonists of Zeneca (ICI, EPA 0 516 297 A1, 02.12.92). Class II compounds are N-oxide derivatives of these compounds and are not disclosed or suggested in the Zeneca patent. The class II compounds are also potent glycine$_B$ antagonists in vitro and show a much better in vivo systemic availability and / or penetration of the blood brain barrier than class I compounds. Moreover, salt derivatives of these compounds, made for example by additon of choline and 4-tetramethylammonium (4-NH$_3$), improve bioavailability further.

The novel compounds of the present invention have predictable utility in the treatment of the following disorders. 1. Acute excitotoxicity such as ischaemia during stroke, trauma, hypoxia, hypoglycaemia and hepatic encephalopathy. 2. Chronic neurodegenerative diseases such as Alzheimer's disease, vascular dementia, Parkinson's disease, Huntington's disease, multiple sclerosis, amyotrophic lateral sclerosis, AIDS-neurodegeneration, olivopontocerebellar atrophy, Tourette's syndrome, motor neurone disease, mitochondrial dysfunction, Korsakoff syndrome, and Creutzfeldt-Jakob disease. 3. Other disorders related to long term plastic changes in the central nervous system such as chronic pain, drug tolerance, dependence and addiction (e.g. opioids, cocaine, benzodiazepines, and alcohol), and tardive dyskinesia. 4. Epilepsy (generalised and partial complex seizures), schizophrenia, anxiety, depression, acute pain, spasticity, and tinnitus.

OBJECTS OF THE INVENTION

It is an object of the invention to provide new and more effective pyrido-phtalazin dione compounds, pharmaceutical compositions thereof, and method of treating neurological disorders associated with excitotoxicity and malfunctioning of glutamatergic neurotransmission therewith. It is a further object of the invention to provide such novel compounds, compositions, and method which fulfill the foregoing theoretical requirements. Additonal objects will become apparent hereinafter, and still other objects of the invention will be apparent to one skilled in the art.

SUMMARY OF THE INVENTION

The invention, then, comprises the following aspects, inter alia, singly or in combination:

A compound selected from those pyridyl-phtalazin diones having the following formula:

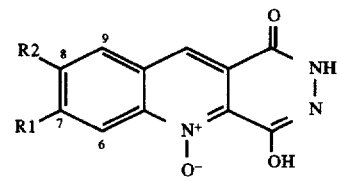

wherein R1 and R2 are selected from the group consisting of hydrogen, halogen, and methoxy or wherein R1 and R2 together form methylenedioxy, and pharmaceutically-acceptable salts thereof; such a compound wherein the salt is selected from a choline and a 4-tetramethyl ammonium salt thereof; such a compound which is selected from the group consisting of 4-hydroxy-1-oxo-1,2-dihydro-pyridazino[4,5-b]-quinoline 5-oxide, 8-chloro-4-hydroxy-1-oxo-1,2-dihydropyridazino[4,5-b)-quinoline 5-oxide, 8-bromo-4-hydroxy-1-oxo-1,2-dihydropyridazino[4,5-b]-quinoline 5-oxide, 8-fluoro-4-hydroxy-1-oxo-1,2-dihydropyridazino[4,5-b]-quinoline 5-oxide, 7,8-dichloro-4-hydroxy-1-oxo-1,2-dihydropyridazino-[4,5-b]-quinoline 5-oxide, 7-bromo-8-chloro-4-hydroxy-1-oxo-1,2-dihydropyridazino-[4,5-b]-quinoline 5-oxide, and 7-chloro-8-bromo-4-hydroxy-1-oxo-1,2-dihydropyridazino-[4,5-b]-quinoline 5-oxide, and a pharmaceutically-acceptable salt of any of the foregoing; and such a compound selected from the group consisting of 4-hydroxy-1-oxo-1,2-dihydro-pyridazino[4,5-b]-quinoline 5-oxide choline salt, 8-chloro-4-hydroxy-1-oxo-1,2-dihydropyridazino[4,5-b]-quinoline 5-oxide choline salt, 8-bromo-4-hydroxy-1-oxo-1,2-dihydropyridazino[4,5-b]-quinoline 5-oxide choline salt, 8-fluoro-4-hydroxy-1-oxo-1,2-dihydropyridazino[4,5-b]-quinoline 5-oxide choline salt, 7,8-dichloro-4-hydroxy-1-oxo-1,2-dihydropyridazino-[4,5-b]-quinoline 5-oxide choline salt, 7-bromo-8-chloro-4-hydroxy-1-oxo-1,2-dihydropyridazino-[4,5-b]-quinoline 5-oxide choline salt, and 7-chloro-8-bromo-4-hydroxy-1-oxo-1,2-dihydropyridazino-[4,5-b]-quinoline 5-oxide choline salt.

Moreover, a pharmaceutical composition containing as active ingredient an effective glycine$_B$ antagonistic amount of such a compound; such a pharmaceutical composition containing as active ingredient an effective glycine$_B$ antagonistic amount of such a compound in the form of a choline salt thereof; such a pharmaceutical composition containing as active ingredient an effective glycine$_B$ antagonistic amount of a compound selected from the group consisting of 4-hydroxy-1-oxo-1,2-dihydro-pyridazino[4,5-b]-quinoline 5-oxide, 8-chloro-4-hydroxy-1-oxo-1,2-dihydropyridazino[4,5-b]-quinoline 5-oxide, 8-bromo-4-hydroxy-1-oxo-1,2-dihydropyridazino[4,5-b]-quinoline 5-oxide, 8-fluoro-4-hydroxy-1-oxo-1,2-dihydropyridazino[4,5-b]-quinoline 5-oxide, 7,8-dichloro-4-hydroxy-1-oxo-1,2-dihydropyridazino-[4,5-b]-quinoline 5-oxide, 7-bromo-8-chloro-4-hydroxy-1-oxo-1,2-dihydropyridazino-[4,5-b]-quinoline 5-oxide, and 7-chloro-8-bromo-4-hydroxy-1-oxo-1,2-dihydropyridazino-(4,5-b]-quinoline 5-oxide, or a pharmaceutically-acceptable salt of any of the foregoing; and such a pharmaceutical composition containing as active ingredient an effective glycine$_B$ antagonistic amount of a compound selected from the group consisting of 4-hydroxy-1-oxo-1,2-dihydro-pyridazino[4,5-b]-quinoline 5-oxide choline salt;

8-chloro-4-hydroxy-1-oxo-1,2-dihydropyridazino[4,5-b]-quinoline 5-oxide choline salt, 8-bromo-4-hydroxy-1-oxo-1,2-dihydropyridazino[4,5-b]-quinoline 5-oxide choline salt, 8-fluoro-4-hydroxy-1-oxo-1,2-dihydropyridazino[4,5-b]-quinoline 5-oxide choline salt, 7,8-dichloro-4-hydroxy-1-oxo-1,2-dihydropyridazino-[4,5-b]-quinoline 5-oxide choline salt, 7-bromo-8-chloro-4-hydroxy-1-oxo-1,2-dihydropyridazino-[4,5-b]-quinoline 5-oxide choline salt, and 7-chloro-8-bromo-4-hydroxy-1-oxo-1,2-dihydropyridazino-[4,5-b]-quinoline 5-oxide choline salt.

Further, a method of combatting neurological disorders associated with excitotoxicity and malfunctioning of glutamatergic neurotransmission in a living animal comprising the step of administering to a living animal in need thereof an effective glycine$_B$ antagonistic amount of such a compound or pharmaceutical composition; such a method wherein the compound is in the form of a choline salt thereof; such a a method wherein the compound is selected from the group consisting of 4-hydroxy-1-oxo-1,2-dihydro-pyridazino[4,5-b]-quinoline 5-oxide, 8-chloro-4-hydroxy-1-oxo-1,2-dihydropyridazino[4,5-b]-quinoline 5-oxide, 8-bromo-4-hydroxy-1-oxo-1,2-dihydropyridazino[4,5-b]-quinoline 5-oxide, 8-fluoro-4-hydroxy-1-oxo-1,2-dihydropyridazino[4,5-b]-quinoline 5-oxide, 7,8-dichloro-4-hydroxy-1-oxo-1,2-dihydropyridazino-[4,5-b]-quinoline 5-oxide, 7-bromo-8-chloro-4-hydroxy-1-oxo-1,2-dihydropyridazino-[4,5-b]-quinoline 5-oxide, and 7-chloro-8-bromo-4-hydroxy-1-oxo-1,2-dihydropyridazino-[4,5-b]-quinoline 5-oxide, or a pharmaceutically-acceptable salt of any of the foregoing; and such a method of combatting neurological disorders associated with excitotoxicity and malfunctioning of glutamatergic neurotransmission in a living animal comprising the step of administering to a living animal in need thereof an effective glycine$_B$ antagonistic amount of a compound selected from the group consisting of 4-hydroxy-1-oxo-1,2-dihydro-pyridazino[4,5-b]-quinoline 5-oxide choline salt, 8-chloro-4-hydroxy-1-oxo-1,2-dihydropyridazino[4,5-b]-quinoline 5-oxide choline salt, 8-bromo-4-hydroxy-1-oxo-1,2-dihydropyridazino[4,5-b]-quinoline 5-oxide choline salt, 8-fluoro-4-hydroxy-1-oxo-1,2-dihydropyridazino[4,5-b]-quinoline 5-oxide choline salt, 7,8-dichloro-4-hydroxy-1-oxo-1,2-dihydropyridazino-[4,5-b]-quinoline 5-oxide choline salt, 7-bromo-8-chloro-4-hydroxy-1-oxo-1,2-dihydropyridazino-[4,5-b]-quinoline 5-oxide choline salt, and 7-chloro-8-bromo-4-hydroxy-1-oxo-1,2-dihydropyridazino-[4,5-b]-quinoline 5-oxide choline salt.

DETAILED DESCRIPTION OF THE INVENTION

The following Discussion, Examples, and Pharmacology are given to illustrate the present invention, but are not to be construed as limiting.

METHODS AND RESULTS

Basic structure of class I and II tricyclic "pyridophtalazin diones"

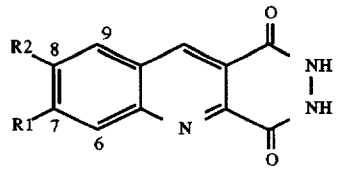

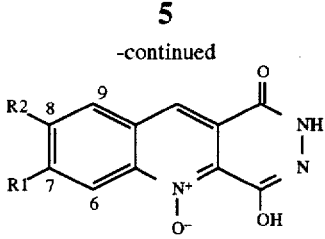

R1/R2=H and/or Halogen
R1/R2=H and/or O—CH₃
R1/R2=H and/or Methylendioxy

CHEMISTRY

General procedure for preparation of dimethyl quinoline-2,3-dicarboxylate 1-oxides (3).

A cold (ice bath) solution of 2-nitrobenzaldehyde 1 (25 mM) and sodium (27 mM) in anhydrous methanol (40 ml) was treated during 30 min with a solution of dimethyl (diethoxyphosphinyl) succinate 2 (30 mM, prepared as described by S. Linke et al., Lieb. Ann. Chem.,1980(4), 542) in anhydrous methanol (10 ml). The resulting dark solution was stirred at 0°–5° C. for 1.5 h, the solvent was evaporated under reduced pressure and the residue partitioned between ethyl acetate and water. The ethyl acetate was dried over sodium sulphate and then evaporated under reduced pressure. The residue was recrystallized from isopropanol to provide the title dimethyl quinoline-2,3-dicarboxylate 1-oxide 3 as an off white (or light yellow) powder.

Physical properties and $^1$H-NMR spectral data of the compounds 3 are given in Tables 1 and 2 a. 5-Bromo-4-chloro-2-nitrobenzaldehyde (1f).

To a mixture of sulphuric acid (40 ml) and sodium nitrate (2.66 g, 31.3 mM) at 0°–5° C. was added 3-bromo-4-chlorobenzaldehyde (6.25 g, 28.5 mM). The resulting mixture was stirred at room temperature for 7 h and then diluted with ice water (300 ml). The precipitated solids were filtered, washed with water and dried to give a powder. Recrystallization of this material from the mixture of isopropanol and water (2:1) provided the title 2-nitrobenzaldehyde 1f (3.6 g, 51.5%) as a light yellow powder, m.p. 81°–82° C.

Analysis for $C_7H_3BrClNO_3$:
Calculated (%): C 31.79 H 1.14 N 5.30
Found (%): C 31.55 H 0.98 N 5.09
$^1$H-NMR (CDCl₃),δ:8.22 (s,1H), 8.23 s,1H),10.39 (s,1H).

b. 4-Bromo-5-chloro-2-nitrobenzaldehyde (1 g).

Using a procedure (a) except starting with 4-bromo-3-chlorobenzaldehyde (2.97 g, 13.5 mM) the title compound 1 g was obtained ( 1.9 g, 53.0%) as a light yellow powder, m.p. 95°–98° C.

Analysis for $C_7H_3BrClNO_3$:
Calculated (%): C 31.79 H 1.14 N 5.30
Found (%): C 31.60 H 1. 01 N 5.1 1
$^1$H-NMR (CDCl₃), δ: 8.02 (s,1H), 8.43 (s,1H), 10.39 (s,1H).

General procedure for preparation of dimethyl quinoline-2,3-dicarboxylates (7).

A solution of N-oxide 3 (10 mM) and phosphorus trichloride (30 mM) in anhydrous chloroform (100 ml) was refluxed for 7 h. Solvent was removed under reduced pressure and the residue was partitioned between ethyl acetate and water. The organic layer was dried over sodium sulphate and then evaporated under reduced pressure. The residue was recrystallized from isopropanol to provide the title dimethyl quinoline-2,3-dicarboxylate 7 as an off white (or light yellow) powder.

Physical properties and $^1$H-NMR spectral data of the compounds 7 are given in Tables 3 and 4.

General procedure for preparation of 4-hydroxy-1-oxo-1,2-dihydropyridazino|4,5-b|-quinoline 5-oxides (5).

To a stirred solution (or suspension) of dimethyl quinoline-2,3-dicarboxylate 1-oxide 3 (5 mM) in boiling ethanol (25 ml) under an argon atmosphere was added hydrazine hydrate (15 mM) and the mixture was refluxed for 3 h during which time a dark precipitate formed. After cooling to room temperature the reaction mixture was filtered and the collected solids were washed with ethanol and ether and dried to provide the hydrazine salt 4. This material was stirred at 70°–110° C. for 3 h in acetic acid (15 ml) and, after cooling to room temperature, the mixture was diluted with water (45 ml) and then filtered to collect the solids. The collected solids were washed with ethanol and dried to provide a dark-yellow solid. Several recrystallizations of this material from dimethylformamide provided the title pyridazino|4,5-b|quinoline 5-oxide 5 as an orange powder.

Physical properties and $^1$H-NMR spectral data of the compounds 5 are given in Tables 5 and 6.

General procedure for preparation of 1,4-dioxo-1,2,3,4-tetrahydropyridazino[4,5-b]-quinolines (9).

To a stirred solution (or suspension) of dimethyl quinoline-2,3-dicarboxylate 7 (5 mM) in boiling ethanol (25 ml) was added hydrazine hydrate (30 mM) and the mixture was refluxed for 8 h during which time a precipitate formed. After cooling to room temperature the reaction mixture was filtered and the collected solids were washed with ethanol and ether and dried to provide the hydrazine salt 8. This material was stirred at 70°–100° C. for 3 h in acetic acid (15 ml) and, after cooling to room temperature, the mixture was diluted with water (45 ml) and then filtered to collect the solids. The collected solids were washed with ethanol and ether and dried to provide the title pyridazino|4,5-b| quinoline 9 as a yellow powder.

Physical properties and $^1$H-NMR spectral data of the compounds 9 are given in Tables 7 and 8.

General procedure for preparation of 4-hydroxy-1-oxo-1,2-dihydropyridazino[4,5-b]-quinoline 5-oxide choline salts (6) and 1,4-dioxo-1,2,3,4-tetrahydropyridazino|4,5-b|-quinoline choline salts (10).

To a stirred suspension of pyridazino[4,5-b]quinoline 9 or N-oxide 5 (10 mM) in methanol (50 ml) was added choline hydroxide (10.5 mM, 45 wt. % solution in methanol). The resulting solution was concentrated using a rotary evaporator and the solid residue was recrystallized from ethanol to provide the title choline salt 10 or 6 as a hygroscopic orange (or red) powder. Physical properties and $^1$H-NMR spectral data of the compounds 6 and 10 are given in Tables 9, 10 and 11, 12 respectively.

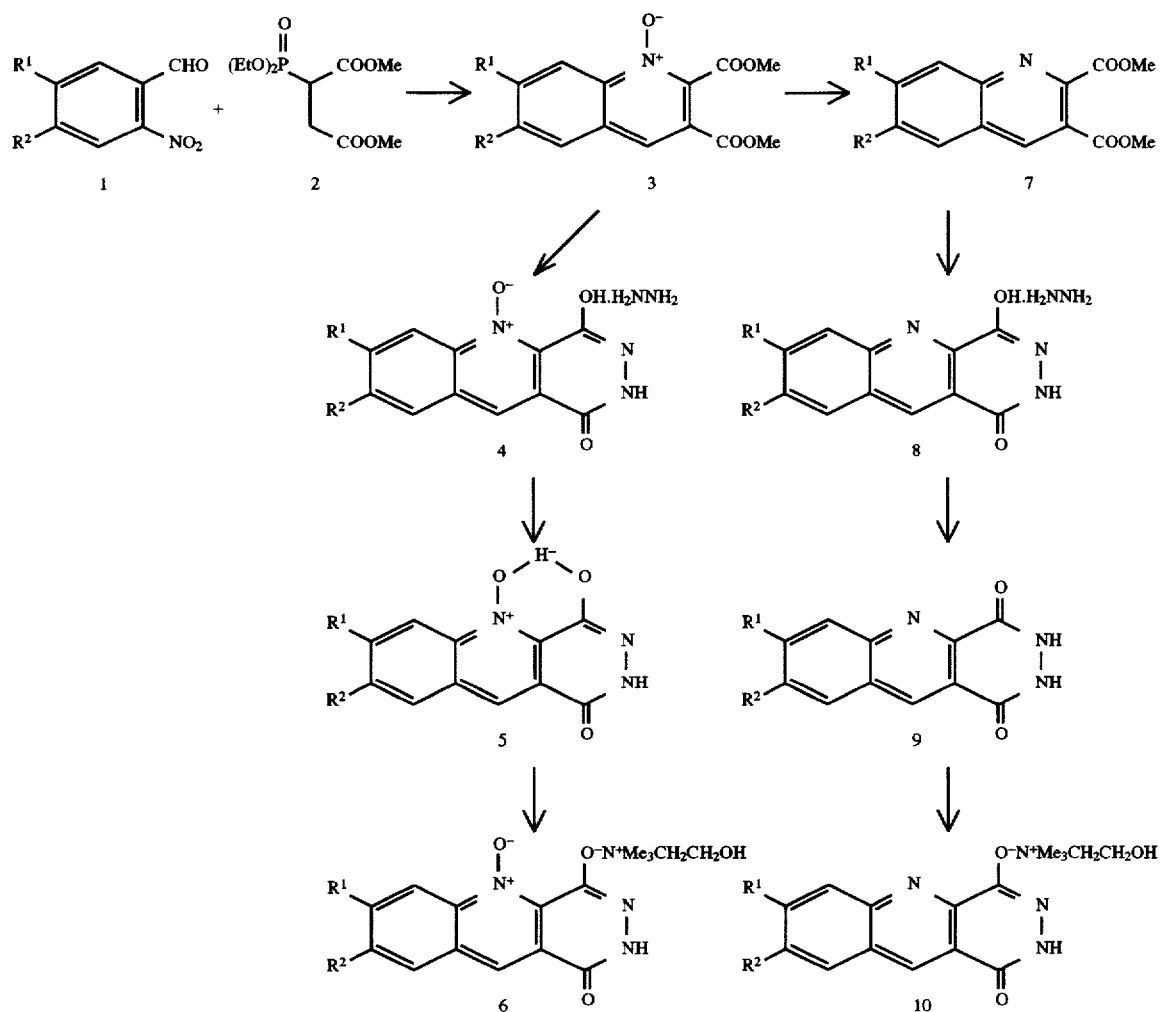
TABLE 1
| | | | Dimethyl quinoline-2,3-dicarboxylate 1-oxides 3 prepared | | | | | | | |
|---|---|---|---|---|---|---|---|---|---|---|
| | | | | Elemental analysis | | | | | | |
| | | | Formula | Calculated (%) | | | Found (%) | | | mp | Yield |
| Compd | $R^1$ | $R^2$ | (mw) | C | H | N | C | H | N | (°C.) | (%) |
| 3a | H | H | $C_{13}H_{11}NO_5$ (261.2) | 59.77 | 4.24 | 5.36 | 59.84 | 4.11 | 5.31 | 175–176 | 61.5 |
| 3b | H | Cl | $C_{13}H_{10}ClNO_5$ (295.7) | 52.81 | 3.41 | 4.74 | 52.80 | 3.32 | 4.78 | 126–127 | 49.0 |
| 3c | H | Br | $C_{13}H_{10}BrNO_5$ (340.2) | 45.89 | 2.96 | 4.11 | 45.57 | 2.75 | 4.00 | 168–170 | 72.0 |
| 3d | H | F | $C_{13}H_{10}FNO_5$ (279.2) | 55.86 | 3.60 | 5.01 | 55.19 | 3.38 | 4.95 | 194–196 | 49.0 |
| 3e | Cl | Cl | $C_{13}H_9Cl_2NO_5$ (330.1) | 47.30 | 2.75 | 4.24 | 47.18 | 2.62 | 4.14 | 183–186 | 41.0 |
| 3f | Cl | Br | $C_{13}H_9BrClNO_5$ (374.6) | 41.69 | 2.42 | 3.74 | 41.39 | 2.13 | 3.65 | 171–173 | 60.0 |
| 3g | Br | Cl | $C_{13}H_9BrClNO_5$ (374.6) | 41.69 | 2.42 | 3.74 | 41.68 | 2.25 | 3.75 | 206–208 | 62.5 |

TABLE 2

$^1$H-NMR (CDCl$_3$) spectral data of compounds 3

| Compd | δ (ppm), J (Hz) |
|---|---|
| 3a | 3.98(s, 3H), 4.11(s, 3H), 7.66–8.05(m, 3H), 8.43(s, 1H), 8.75(dd, J$_1$=8.5, J$_2$=2.0, 1H) |
| 3b | 3.98(s, 3H), 4.11(s, 3H), 7.71(dd, J$_1$=8.5, J$_2$=2.5, 1H), 7.91(d, J=8.5, 1H), 8.38(s, 1H), 8.74(d, J=2.5, 1H) |
| 3c | 3.91(s, 3H), 4.07(s, 3H), 7.13(dd, J$_1$=9.5, J$_2$=2.0, 1H), 7.44(d, J=2.0, 1H), 8.22(s, 1H), 8.58(d, J=9.5, 1H) |
| 3d | 3.98(s, 3H), 4.11(s, 3H), 7.48–7.72(m, 2H), 8.31(s, 1H), 8.73(dd, J$_1$=10.0, J$_2$=5.0, 1H) |
| 3e | 3.97(s, 3H), 4.10(s, 3H), 8.08(s, 1H), 8.28(s, 1H), 8.83(s, 1H) |
| 3f | 3.97(s, 3H), 4.09(s, 3H), 8.26(s, 2H), 8.82(s, 1H) |
| 3g | 3.97(s, 3H), 4.09(s, 3H), 8.06(s, 1H), 8.27(s, 1H),(02 9s, 1H) |

TABLE 3

Dimethyl quinoline-2,3-dicarboxylates 7 prepared

| Compd | R$^1$ | R$^2$ | Formula (mw) | Calculated (%) C | H | N | Found (%) C | H | N | mp (°C.) | Yield (%) |
|---|---|---|---|---|---|---|---|---|---|---|---|
| 7a | H | H | C$_{13}$H$_{11}$NO$_4$ (245.2) | 63.67 | 4.52 | 5.71 | 63.48 | 4.52 | 5.63 | 104–106 | 88.0 |
| 7b | H | Cl | C$_{13}$H$_{10}$ClNO$_4$ (279.7) | 55.83 | 3.60 | 5.01 | 55.74 | 3.59 | 5.00 | 152–154 | 90.0 |
| 7c | H | Br | C$_{13}$H$_{10}$BrNO$_4$ (324.1) | 48.17 | 3.11 | 4.32 | 48.09 | 3.05 | 4.26 | 155–157 | 81.5 |
| 7d | H | F | C$_{13}$H$_{10}$FNO$_4$ (263.2) | 59.32 | 3.83 | 5.32 | 59.23 | 3.79 | 5.26 | 119–121 | 85.0 |
| 7e | Cl | Cl | C$_{13}$H$_9$Cl$_2$NO$_4$ (314.1) | 49.71 | 2.89 | 4.46 | 49.56 | 2.85 | 4.41 | 113–115 | 96.0 |
| 7f | Cl | Br | C$_{13}$H$_9$BrClO$_4$ (348.6) | 43.55 | 2.53 | 3.91 | 43.60 | 2.48 | 3.88 | 128–130 | 95.0 |
| 7g | Br | Cl | C$_{13}$H$_9$BrClO$_4$ (348.6) | 43.55 | 2.53 | 3.91 | 43.47 | 2.51 | 3.87 | 142–144 | 67.0 |

TABLE 4

$^1$H-NMR (CDCl$_3$) spectral data of compounds 7

| Compd | δ (ppm), J (Hz) |
|---|---|
| 7a | 3.98(s, 3H), 4.06(s, 3H), 7.58–8.00(m, 3H), 8.21(dd, J$_1$=9.5, J$_2$=2.0, 1H), 8.77(m, 2H), 8.77(s, 1H) |
| 7b | 3.97(s, 3H), 4.06(s, 3H), 7.76(dd, J$_1$=9.5, J$_2$=2.0, 1H), 7.90(d, J=2.0, 1H), 8.67(s, 1H) |
| 7c | 3.97(s, 3H), 4.07(s, 3H), 7.90(dd, J$_1$=9.5, J$_2$=2.0, 8.09(m, 2H), 8.66(s, 1H) |
| 7d | 3.98(s, 3H), 4.07(s, 3H), 7.49–7.72(m, 2H), 8.20(dd, J$_1$=10, J$_2$=5.0, 1H), 8.69(s, 1H) |
| 7e | 3.97(s, 3H), 4.04(s, 3H), 8.02(s, 1H), 8.31(s, 1H), 8.64(s, 1H) |
| 7f | 3.98(s, 3H), 4.06(s, 3H), 8.24(s, 1H), 8.33(s, 1H), 8.68(s, 1H) |
| 7g | 3.96(s, 3H), 4.04(s, 3H), 8.03(s, 1H), 8.53(s, 1H), 8.62(s, 1H) |

TABLE 5

4-Hydroxy-1-oxo-1,2-dihydropyridazino[4,5-b]quinoline 5-oxides 5 prepared

| Mrz 2/ | Compd | R¹ | R² | Formula (mw) | Calculated (%) C | H | N | Found (%) C | H | N | mp (°C.) | Yield (%) |
|---|---|---|---|---|---|---|---|---|---|---|---|---|
| 499 | 5a | H | H | $C_{11}H_7N_3O_3$ (229.2) | 57.65 | 3.08 | 18.33 | 57.56 | 2.93 | 18.22 | >300 | 44.5 |
| 502 | 5b | H | Cl | $C_{11}H_6ClN_3O_3$ (263.6) | 50.11 | 2.29 | 15.94 | 49.34 | 2.29 | 15.40 | >300 | 88.0 |
| 514 | 5c | H | Br | $C_{11}H_6BrN_3O_3$ (308.1) | 42.88 | 1.96 | 13.63 | 42.57 | 1.91 | 13.49 | >300 | 78.0 |
| 516 | 5d | H | F | $C_{11}H_6FN_3O_3$ (247.2) | 55.44 | 2.44 | 16.99 | 53.44 | 2.35 | 16.90 | 297–298 | 37.0 |
| 518 | 5e | Cl | Cl | $C_{11}H_5Cl_2N_3O_3$ (298.1) | 44.32 | 1.69 | 14.10 | 44.17 | 1.91 | 14.34 | >300 | 16.0 |
| 551 | 5f | Cl | Br | $C_{11}H_5BrClN_3O_3$ (342.5) | 38.57 | 1.47 | 12.27 | 37.93 | 1.33 | 11.94 | >300 | 15.0 |
| 568 | 5g | Br | Cl | $C_{11}H_5BrClN_3O_3$ (342.5) | 38.57 | 1.47 | 12.27 | 38.17 | 1.31 | 12.00 | >300 | 17.0 |

TABLE 6

¹H-NMR (DMSO-d₆) spectral data of compounds 5

δ (ppm), J (Hz)

| Compd | aromatic protons (and OCH₃) | NH, OH (exchangeable) |
|---|---|---|
| 5a | 7.88–8.28(m, 2H), 8.46–8.79(m, 2H), 9.07(s, 1H) | 10.65(br.s, 1H), 12.00(br.s, 1H) |
| 5b | 8.07(dd, J₁=9.0, J₂=2.5, 1H), 8.59(d, J=9.0, 1H), 8.69(d, J=2.5, 1H), 9.11(s, 1H) | 12.05(br.s, 1H), 14.60(br.s, 1H) |
| 5c | 8.27(dd, J₁=9.0, J₂=2.0, 1H), 8.60(d, J=9.0, 1H), 8.82(d, J=2.0, 1H), 9.00(s, 1H) | 11.00(br.s, 1H), 12.00(br.s, 1H) |
| 5d | 8.07 (ddd, J₁=9.5, J₂=8.5, J₃=2.5, 1H), 8.36(dd, J₁=9.5, J₂=2.5, 1H), 8.75(dd, J₁=9.5, J₂=5.0, 1H), 9.02(s, 1H) | 10.92(br.s, 1H), 12.00(br.s, 1H) |
| 5e | 8.83(s, 1H), 8.90(s, 1H), 9.06(s, 1H) | 11.25(br.s, 1H), 12.05(br.s, 1H) |
| 5f | 8.80(s, 1H), 9.00(s, 1H), 9.01(s, 1H) | 12.06(br.s, 1H), 14.28(br.s, 1H) |
| 5g | 8.90(s, 1H), 9.01(s, 1H), 9.04(s, 1H) | 12.13(br.s, 1H), 14.32(br.s, 1H) |

TABLE 7

1,4-Dioxo-1,2,3,4-tetrahydropyridazino[4,5-b]quinolines 9 prepared

| Mrz 2/ | Compd | R¹ | R² | Formula (mw) | Calculated (%) C | H | N | Found (%) C | H | N | mp (°C.) | Yield (%) |
|---|---|---|---|---|---|---|---|---|---|---|---|---|
| 585 | 9a | H | H | $C_{11}H_7N_3O_2$ (213.2) | 61.97 | 3.31 | 19.71 | 61.43 | 3.45 | 19.16 | >300 | 86.0 |
| 501 | 9b | H | Cl | $C_{11}H_6ClN_3O_2$ (247.6) | 53.35 | 2.44 | 16.97 | 32.89 | 2.28 | 16.68 | >309 | 88.5 |
| 503 | 9c | H | Br | $C_{11}H_6BrN_3O_2$ (292.1) | 45.23 | 2.07 | 14.39 | 44.74 | 2.11 | 14.09 | >300 | 82.0 |
| 519 | 9d | H | F | $C_{11}H_6FN_3O_2$ (231.2) | 57.14 | 2.60 | 18.18 | 56.73 | 2.47 | 17.99 | >300 | 84.0 |
| 515 | 9e | Cl | Cl | $C_{11}H_5Cl_2N_3O_2$ (282.1) | 46.84 | 1.79 | 14.90 | 46.44 | 1.70 | 14.87 | >300 | 82.5 |

TABLE 7-continued

1,4-Dioxo-1,2,3,4-tetrahydropyridazino[4,5-b]quinolines 9 prepared

| Mrz 2/ | Compd | R¹ | R² | Formula (mw) | Calculated (%) C | Calculated (%) H | Calculated (%) N | Found (%) C | Found (%) H | Found (%) N | mp (°C.) | Yield (%) |
|---|---|---|---|---|---|---|---|---|---|---|---|---|
| 539 | 9f | Cl | Br | $C_{11}H_5BrClN_3O_2$ (326.5) | 40.46 | 1.54 | 12.87 | 40.16 | 1.42 | 12.88 | >300 | 69.5 |
| 538 | 9g | Br | Cl | $C_{11}H_5BrClN_3O_2$ (326.5) | 40.46 | 1.54 | 12.87 | 40.23 | 1.40 | 12.98 | >300 | 88.0 |

TABLE 8

¹H-NMR (DMSO-d₆) spectral data of compounds 9

| Compd | aromatic protons δ (ppm), J (Hz) | NH (exchangeable) |
|---|---|---|
| 9a | 7.76–8.16(m, 2H), 8.22–8.47(m, 2H), 9.30(s, 1H) | 11.60(br.s, 2H) |
| 9b | 8.02(dd, J₁=9.0, J₂=2.5, 1H), 8.28(d, J=9.0, 1H), 8.52(d, J=2.5, 1H), 9.26(s, 1H) | 11.60(br.s, 2H) |
| 9c | 8.16(m, 2H), 8.60(br.s, 1H), 9.25(s, 1H) | 11.55(br.s, 2H) |
| 9d | 7.93(ddd, J₁=9.5, J₂(H,F)=9.0, J₃=2.5, 1H), 8.18(dd, J₁(H,F)=9.5, J₂=2.5, 1H), 8.36(dd, J₁=9.5, J₂(H,F)=5.5, 1H), 9.24(s, 1H) | 11.90(br.s, 2H) |
| 9e | 8.47(s, 1H), 8.67(s, 1H), 9.22(s, 1H) | 11.60(br.s, 2H) |
| 9f | 8.52(s, 1H), 8.91(s, 1H), 9.28(s, 1H) | 11.65(br.s, 2H) |
| 9g | 8.68(s, 1H), 8.71(s, 1H), 9.26(s, 1H) | 11.70(br.s, 2H) |

TABLE 9

4-Hydroxy-1-oxo-1,2-dihydropyridazino[4,5-b]quinoline 5-oxide choline salts 6 prepared

| Mrz 2/ | Compd | R¹ | R² | Formula (mw) | Calculated for 6 × H₂O* (%) C | Calculated for 6 × H₂O* (%) H | Calculated for 6 × H₂O* (%) N | Found (%) C | Found (%) H | Found (%) N | mp (°C.) | Yield (%) |
|---|---|---|---|---|---|---|---|---|---|---|---|---|
| 577 | 6a | H | H | $C_{16}H_{20}N_4O_4$ (332.4) | 54.84 | 6.32 | 15.99 | 54.76 | 6.32 | 15.86 | 179–180 | 52.5 |
| 576 | 6b | H | Cl | $C_{16}H_{19}ClN_4O_4$ (366.8) | 49.93 | 5.50 | 14.55 | 49.31 | 5.47 | 14.24 | 185–188 | 87.5 |
| 570 | 6c | H | Br | $C_{16}H_{19}BrN_4O_4$ (411.4) | 44.75 | 4.92 | 13.04 | 44.85 | 4.93 | 12.36 | 191–193 | 71.5 |
| 571 | 6d | H | F | $C_{16}H_{19}FN_4O_4$ (366.4) | 51.19 | 5.63 | 14.92 | 51.74 | 5.73 | 14.95 | 201–203 | 27.0 |
| 574 | 6e | Cl | Cl | | | | | | | | | |
| | 6f | Cl | Br | | | | | | | | | |
| | 6g | Br | Cl | | | | | | | | | |

*x = 1.0 (a, b, c)
0.5 (d)

TABLE 10

$^1$H-NMR (CD$_3$OD) spectral data of choline salts 6

δ (ppm), J (Hz)

| Compd. | choline protons | aromatic protons |
|---|---|---|
| 6a | 3.20(s, 9H), 3.47(m, 2H), 3.98(m, 2H) | 7.69–8.00(m, 2H), 8.18(d, J=8.0, 1H), 8.59(s, 1H), 8.76(d, J=8.5, 1H) |
| 6b | 3.22(s, 9H), 3.50(m, 2H), 4.01(m, 2H) | 7.88(dd, J$_1$=9.0, J$_2$=2.5, 1H), 8.27(d, J=2.5, 1H), 8.52(s, 1H), 8.76(d, J=9.0, 1H) |
| 6c | 3.20(s, 9H), 3.48(m, 2H), 3.99(m, 2H) | 7.99(dd, J$_1$=9.5, J$_2$=2.0, 1H), 8.41(d, J=2.0, 1H), 8.53(s, 1H), 8.64(d, J=9.5, 1H) |
| 6d | 3.22(s, 9H), 3.51(m, 2H), 4.02(m, 2H) | 7.64–7.98(m, 2H), 8.62(s, 1H), 8.87(dd, J$_1$=10.0, J$_2$=5.0, 1H) |
| 6e | | |
| 6f | | |
| 6g | | |

TABLE 11

1,4-Dioxo-1,2,3,4-tetrahydropyridazino[4,5-b]quinoline choline salts 10 prepared

| | | | | | Elemental analysis | | | | | | |
|---|---|---|---|---|---|---|---|---|---|---|---|
| | | | | Calculated for 6 × H$_2$O* (%) | | | Found (%) | | | | |
| Mrz 2/ | Compd | R$^1$ | R$^2$ | Formula (mw) | C | H | N | C | H | N | mp (°C.) | Yield (%) |
| 604 | 10a | H | H | C$_{16}$H$_{20}$N$_4$O$_3$ (316.36) | 54.26 | 7.59 | 14.06 | 54.23 | 7.39 | 14.25 | 102–110 | 82.0 |
| 596 | 10b | H | Cl | C$_{16}$H$_{19}$ClN$_4$O$_3$ (350.8) | 54.08 | 5.53 | 15.76 | 54.10 | 5.55 | 15.61 | 189–191 | 84.0 |
| 586 | 10c | H | Br | C$_{16}$H$_{19}$BrN$_4$O$_3$ (395.3) | 43.64 | 5.49 | 12.72 | 44.07 | 5.14 | 12.73 | 234–236 | 61.0 |
| 572 | 10d | H | F | C$_{16}$H$_{19}$FN$_4$O$_3$ (334.4) | 52.16 | 15.20 | 5.74 | 52.08 | 6.23 | 15.19 | 229–230 | 95.0 |
| 574 | 10e | Cl | Cl | C$_{16}$H$_{18}$Cl$_2$N$_4$O$_3$ (385.3) | 47.65 | 4.99 | 13.89 | 47.24 | 5.03 | 13.60 | 205–208 | 83.0 |
| 598 | 10f | Cl | Br | C$_{16}$H$_{18}$BrClN$_4$O$_3$ (429.7) | 42.92 | 4.5 | 12.51 | 42.78 | 4.60 | 12.44 | 207–209 | 92.0 |
| 597 | 10g | Br | Cl | C$_{16}$H$_{18}$BrClN$_4$O$_3$ (429.7) | 42.92 | 4.5 | 12.51 | 42.66 | 4.57 | 12.37 | 201–203 | 95.0 |

*x = 0.25 (d)
1.0 (d,e)
2.5 (c)

TABLE 12

$^1$H-NMR (CD$_3$OD) spectral data of choline salts 10

δ (ppm), J (Hz)

| Compd. | choline protons | aromatic protons |
|---|---|---|
| 10a | 3.21(s, 9H), 3.51(m, 2H), 4.01(m, 2H) | 7.64–8.57(m, 4H), 9.17(s, 1H) |
| 10b | 3.25(s, 9H), 3.52(m, 2H), 4.02(m, 2H) | 7.89(dd, J$_1$=9.0, J$_2$=2.5, 1H), 8.23(d, J=2.5, 1H), 8.34(d, J=9.0, 1H), 9.13(s, 1H) |
| 10c | 3.22(s, 9H), 3.47(m, 2H), 3.97(m, 2H) | 7.99(dd, J$_1$=9.0, J$_2$=2.0, 1H), 8.26(d, J=9.0, 1H), 8.41(d, J=2.0, 1H), 9.09(s, 1H) |
| 10d | 3.20(s, 9H), 3.49(m, 2H), 3.98(m, 2H) | 7.64–7.81(m, 2H), 8.39(dd, J$_1$=9.5, J$_2$=5.0, 1H), 9.12(s, 1H) |
| 10e | 3.22(s, 9H), 3.51(m, 2H), 4.02(m, 2H) | 8.46(s, 1H), 8.55(s, 1H), 9.14(s, 1H) |
| 10f | 3.22(s, 9H), 3.50(m, 2H), | 8.53(s, 1H), 8.64(s, 1H), |

TABLE 12-continued

$^1$H-NMR (CD$_3$OD) spectral data of choline salts 10

δ (ppm), J (Hz)

| Compd. | choline protons | aromatic protons |
|---|---|---|
| | 4.00(m, 2H) | 9.13(s, 1H) |
| 10g | 3.22(s, 9H), 3.50(m, 2H), 4.02(m, 2H) | 8.43(s, 1H), 8.73(s, 1H), 9.13(s, 1H) |

PHARMACOLOGY

In vitro
Receptor Binding Studies
Membrane preparation and protein determination Tissue preparation was performed according to Foster and Wong (1987). Male Sprague-Dawley rats (200–250g) were decapitated and their brains were removed rapidly. The cortex was dissected and homogenised in 20 volumes of ice-cold 0.32M sucrose using a glass-Teflon homogenizer. The homogenate was centrifuged at 1000×g for 10 min. The pellet was discarded and the supernatant centrifuged at 20,000×g for 20 min. The resulting pellet was resuspended in 20 volumes of distilled water and centrifuged for 20 min at 8000×g. Then the supernatant and the buffy coat were centrifuged three times (48,000× g for 20 min) in the presence of 5 mM Tris-HCl, pH 7.4. All centrifugation steps were carried out at 4° C. After resuspension in 5 volumes of 5 mM Tris-HCl, pH 7.4 the membrane suspension was frozen rapidly at −80° C. until the day of assay. On the day of assay the membranes were thawed and washed four times by resuspension in 5 mM Tris-HCl, pH 7.4 and centrifugation at 48,000× g for 20 min. The final pellet was suspended in assay buffer.

The amount of protein in the final membrane preparation was determined according to the method of Lowry (1951) with some modifications (Hartfree, 1972). 50 μl of Protein samples (in triplicates) were diluted to 1 ml with distilled water and treated with 0.9 ml of a solution containing 2 g potassium sodium tartrate and 10 g Na$_2$CO$_3$ in 500 ml 1N NaOH and 500ml water. Blank and standard (with bovine serum albumin) were set up in the same way. The tubes were placed in a water bath at 50° C. for 10 min. and cooled at room temperature. 100 µl of a solution containing 2 g potassium sodium tartrate and 1 g $CuSO_4 \times 5\ H_2O$ in 90 ml water and 10 ml 1N NaOH were added. The samples were left at room temperature for at least 10 min., then 3 ml of Folin-Ciocalteu reagent (1 ml of reagent diluted with 15 ml water) was added rapidly during mixing. The tubes were again heated at 50° C. for 10 min. and cooled to room temperature. Absorbencies were then read in 1 cm cuvets at 650 nm. The final protein concentration used for our studies was between 100 and 250 µg/ml.

Incubation in both binding assays was terminated using a Millipore filter system. The samples, all in triplicate, were rinsed three times with 2.5 ml ice cold assay buffer over glass fibre filters obtained from Schleicher & Schuell under a constant vacuum. Following separation and rinse the filters were placed into scintillation liquid (5 ml; Ultima Gold) and radioactivity retained on the filters was determined by using conventional liquid scintillation counter (Hewlett Packard, Liquid Scintillation Analyser). 'Total binding' was the absolute amount of radioligand bound in the absence of any additives whereas 'non-specific' binding was determined in the presence of a high concentration of competitor.

[$^3$H]5,7-DCKA binding assay

Experiments were performed according to the methods modified from previous groups (Canton et al., 1991; Yoneda et al., 1993). Membranes were suspended and incubated in 10 mM Tris-HCl, pH 7.4. Incubation time was 45 min at 4° C. Non-specific binding of [$^3$H]5,7-DCKA was defined by the addition of unlabeled glycine at 0.1 mM. The stop-solution contained 10 mM Tris-HCl and 10 mM magnesium sulphate, pH 7.4. Filtration was performed as rapidly as possible. Displacement experiments were performed with a fixed [$^3$H]5,7-DCKA concentration of 10 nM. Test compounds were diluted in water or DMSO and added in at least 5 different concentrations.

[$^3$H]glycine binding assay

[$^3$H]glycine binding assays were performed according to the method described by Kessler and co-workers (1989). Rat cortical membranes were prepared as previously described and the final pellet was suspended in 50 mM Tris-acetate, pH 7.4. At least 5 different concentrations of test compounds were incubated with 2OnM [$^3$H]glycine for 30 min at 4° C. in the presence of 100 µM strychnine. All compounds were dissolved in water or DMSO, respectively. Non-specific binding was determined by including 100 µM glycine in the incubation mixture. The incubation was terminated by diluting the samples with 2 ml of stop solution (50 mM Tris-HCl including 10 mM magnesium sulphate, pH 7.4, cooled to <2° C.) followed by a further rinse with 2.5 ml buffer. Filtration was performed as rapidly as possible.

Results

Eight of the tested compounds had IC$_{50}$s in the [$^3$H]-DCKA assay≦1 µM (see table 13). The potency of six selected compounds in the [$^3$H]-glycine assay appears at first sight to be greater but this is not reflected in large differences in Kds (not shown). Of the pairs of compounds of particular interest, class II compounds had a greater affinity than class I compounds in the [$^3$H]-DCKA assay. This difference was not so evident in the [$^3$H]-glycine assay.

TABLE 13a

| Mrz 2/ | Substance | [$^3$H] DCKA IC$_{50}$ µM | [$^3$H] Glycine IC$_{50}$ µM |
| --- | --- | --- | --- |
| 499 | II | 16.0 | |
| 501 | 8-Cl-I | 0.120 | 0.080 |
| 502 | 8-Cl-II | 0.020 | 0.013 |
| 503 | 8-Br-I | 0.250 | 0.013 |
| 514 | 8-Br-II | 0.010 | 0.004 |
| 519 | 8-F-I | 1.100 | 0.015 |
| 516 | 8-F-II | 0.300 | 0.017 |
| 515 | 7,8-DiCl-I | 0.530 | |
| 518 | 7,8-DiCl-II | 0.650 | |

TABLE 13b

| Mrz 2/ | Substance | [$^3$H] DCKA IC$_{50}$ µM |
| --- | --- | --- |
| 572 | 8-F-I (Chol) | 1.14 |
| 571 | 8-F-II (Chol) | 0.32 |
| 569 | 8-Cl-I (Chol) | 0.97 |
| 576 | 8-Cl-II (Chol) | 0.45 |

Patch clamp
Methods

Superior colliculi were obtained from rat embryos (E20 to E21) and were then transferred to calcium and magnesium free Hank's buffered salt solution (Gibco) on ice. Cells were mechanically dissociated in 0.05% DNAase / 0.3% ovomucoid (Sigma) following a 15 minute pre-incubation with 0.66% trypsin / 0.1% DNAase (Sigma). The dissociated cells were then centrifuged at 18G for 10 minutes, resuspended in minimum essential medium (Gibco) and plated at a density of 200.000 cells cm onto poly-L-lysine (Sigma)-precoated plastic petri dishes (Falcon). The cells were nourished with NaHCO$_3$/HEPES-buffered minimum essential medium supplemented with 5% foetal calf serum and 5% horse serum (Gibco) and incubated at 37° C. with 5%CO$_2$ at 95% humidity. The medium was exchanged completely following inhibition of further glial mitosis with cytosine-β-D-arabinofuranoside (20 µM Sigma) after about 7 days in vitro. Thereafter the medium was exchanged partially twice weekly. The superior colliculus culture was chosen for these experiments as it provides very stable recording conditions which are an absolute prerequisite for voltage-dependency and kinetic experiments. Moreover, the relatively small neurones (soma 15-20 µm ϕ) are ideally suited to minimise problems of buffered diffusion for concentration clamp experiments.

Patch clamp recordings were made from these neurones with polished glass electrodes (4-6 mΩ) in the whole cell mode at room temperature (20°-22° C.) with the aid of an EPC-7 amplifier (List). Test substances were applied by switching channels of a custom made fast superfusion system with a common outflow (10-20 ms exchange times). The contents of the intracellular solution were as follows (mM): CsCl (120), TEACl (20), EGTA (10), MgCl$_2$ (1), CaCl$_2$ (0.2), glucose (10), ATP (2), cAMP (0.25); pH was adjusted to 7.3 with CsOH or HCl. The extracellular solutions had the following basic composition (mM): NaCl (140), KCl (3), CaCl$_2$ (0.2), glucose (10), HEPES (10), sucrose (4.5), tetrodotoxin (TTX 3*10-4). For most experiments glycine (1 µM) was present in all solutions. Experiments to test the glycine-dependence of the tricyclic "pyrido-phtalazin diones" were performed in the continuous presence of increasing concentrations of glycine (1-10 µM).

Results

Five pairs of tricyclic "pyrido-phtalazin diones" had $IC_{50}$s against inward currents to NMDA (200 μM) in the low μM range and class II compounds were generally about 2–3 times more potent than class I compounds (table 14a). The most potent of these were Mrz 2/502 and Mrz 2/514. This effect was mediated at the glycine$_B$ site as evidenced by the parallel shift in the concentration-response curves in the presence of increasing glycine concentrations. Thus the Kbs of Mrz 2/502 as assessed according to the Cheng-Prusoff relationship were similar in glycine 1, 3 and 10 μM (80, 124 and 118 nM respectively). Furthermore, the effects of Mrz 2/501 and 2/502 were not voltage-dependent. All compounds tested were about three to ten times more potent against steady-state currents than against peak currents. Choline derivatives had similar potencies to the free acids in vitro (Table 14b).

In contrast, three of these potent glycine, antagonists were only very weak antagonists of inward currents to AMPA (100 μM). Mrz 2/502, 2/514 and 2/516 had $IC_{50}$s against peak AMPA induced currents of 25, 73 and 18 μm respectively but were essentially inactive against plateau currents all $IC_{50}$s>100 μM (table 14a). This profile of action, although very weak, is typical for competitive AMPA receptor antagonists which preferentially block the peak non-desensitised state, low affinity state of the receptor (see Parsons et al., 1994).

TABLE 14a

| Mrz 2/ | Substance | Peak NMDA $IC_{50}$ μM | Plateau NMDA $IC_{50}$ μM | Peak AMPA $IC_{50}$ μM | Plateau AMPA $IC_{50}$ μM |
|---|---|---|---|---|---|
| 585 | I | 65.9 | 19.1 | | |
| 499 | II | 51.2 | 13.8 | | |
| 501 | 8-Cl-I | 2.3 | 0.7 | | |
| 502 | 8-Cl-II | 0.8 | 0.3 | 25.0 | 150.0 |
| 503 | 8-Br-I | 1.7 | 0.6 | | |
| 514 | 8-Br-II | 0.5 | 0.2 | 72.7 | 307.0 |
| 519 | 8-F-I | 18.0 | 5.8 | | |
| 516 | 8-F-II | 6.3 | 1.6 | 17.6 | >100 |
| 515 | 7,8-DiCl-I | 3.7 | 0.9 | | |
| 518 | 7,8-DiCl-II | 3.8 | 0.8 | | |
| 539 | 7-Cl,8-Br-I | 5.3 | 0.7 | | |
| 551 | 7-Cl,8-Br-II | 2.4 | 0.6 | | |
| 538 | 7-Br,8-Cl-I | 93.9 | 2.5 | | |
| 568 | 7-Br,8-Cl-II | 10.0 | 1.5 | | |
| 554 | 8-O-CH$_3$-I | 170 | 36.2 | | |

TABLE 14b

| Mrz 2/ | Substance | Peak NMDA $IC_{50}$ μM | Plateau NMDA $IC_{50}$ μM |
|---|---|---|---|
| 569 | 8-Cl-I (Chol) | 2.0 | 0.5 |
| 576 | 8-Cl-II (Chol) | 1.1 | 0.5 |
| 586 | 8-Br-I (Chol) | 2.2 | 0.6 |
| 570 | 8-Br-II (Chol) | 0.6 | 0.1 |
| 572 | 8-F-I (Chol) | 12.4 | 3.5 |
| 571 | 8-F-II (Chol) | 4.9 | 1.0 |
| 578 | 8-O-CH$_3$-II (Chol) | 101 | 7.7 |
| 575 | 7-O-CH$_3$-I (Chol) | 94.0 | 14.5 |

Excitotoxicity in vitro
Methods

Isolation of cortical neurones was similar to that described for patch clamp recordings except for the use of foetal rats at 17–19 days gestation. Neurones were plated in 24-multiwell (Greiner) at a density of 300,000 cells/well coated with poly-D-lysine 0.025 mg/ml. Cells were cultured in Dulbecco's modified essential medium (DMEM, GIBCO) supplemented with 10% heat inactivated foetal calf serum (GIBCO). Cultures were maintained at 37° C. at 5% $CO_2$. The medium was changed first after one week and then every 3 days by replacing half of the medium with fresh medium. Cultures aged 17 days were used for experiments.

Exposure to EAA was performed in serum-free MEM-N2 medium (Bottenstein 1979) containing 0.5 mM NMDA/1 μM glycine and the drug to be tested. Cells were pre-incubated with drugs and 1 μM glycine for 15 minutes before addition of NMDA. After 24 h the cytotoxic effect was morphologically examined under a phase contrast microscope and biochemically quantitified by measuring the efflux of LDH.

The activity of LDH was determined in the supernatant after 24 h according to the method of Wroblewski and La Due (1955). Briefly, 0.1 ml of the supernatant was added to 0.9 ml sodium-phosphate buffer (pH=7.5) containing sodium pyruvate (22.7 mM) and NADH (0.8 mg/10 ml) at room temperature. The conversion of pyruvate to lactate was recorded at 340 nm over 10 minutes in a Kontron Spectrophotometer.

Results

Full concentration-response curves are not yet available. However, low μM concentrations of Mrz 2/501 and Mrz 2/502 were effective neuroprotectants in vitro, with Mrz 2/502 seeming to be more potent in this regard (see table 15).

TABLE 15

| Mrz 2/ | Substance | Cytotoxicity in vitro $IC_{50}$ μM |
|---|---|---|
| 501 | 8-Cl-I | <5 |
| 502 | 8-Cl-II | <<5 |
| 503 | 8-Br-I | >20 |

In vivo
Anticonvulsive activity
Aim

To assess NMDA receptor antagonistic properties of the tested agents by assessing anticonvulsive effects. Additionally the role of organic acid transporters in the elimination from the brain of tested agents was assessed by using an inhibitor, Probenicid, on the duration of anticonvulsive activity.

Methods

Male albino Swiss mice (19–21 g) housed 10–15 per cage were used for the NMDA lethality test (Leander et al., 1988). For pentylenetetrazol (PTZ)-induced convulsions male albino Swiss mice (25–34 g.) housed 40 per cage (58×38×20 cm) were used while in the maximal electroshock (MES) and motor impairment tests NMR female mice (18–28 g) housed 5 per cage were employed. All animals were kept with water and food ad libittum under a 12-h light-dark cycle (light on at 6 a.m.), and at a controlled temperature (20°±0.5° C.). All experiments were performed between 10 a.m. and 5 p.m. Tested agents were injected 15 min. i.p before the induction of convulsions if not stated otherwise (see below). Mrz 2/502 was dissolved in saline added with NaOH. Most other agents were dissolved in the following solution: 0.606 g Tris; 5.0 g. glucose; 0.5 g. Tween 80; and 95 ml water. The choline and tetramethylammonium salts were dissolved in distilled water.

In the NMDA-induced convulsions test in mice, a dose-response relationship for NMDA was first performed to determine the $ED_{97}$ dose which was then used for testing of antagonistic properties. After injection of the $ED_{97}$ dose of NMDA the animals were placed in a small cage (20×28×14 cm) and observed for 20 min. Death preceded by clonic convulsions and by tonic seizures was the pharmacological end-point.

Pentylenetetrazol was injected at a dose of 90 mg/kg (i.p). The presence of general tonic convulsions was then scored for 30 min as this parameter is more sensitive to NMDA receptor antagonists than clonic convulsions. The pharmacological end-point was taken as the presence of tonus in the hind limbs with stretching.

MES (100 Hz, 0.5 sec shock duration, 50 mA shock intensity, 0.9 ms impulse duration, Ugo Basile) was applied through corneal electrodes. The presence of tonic convulsions was scored (tonic extension of hind paws with minimum angle to the body of 90°). In an additional experiment mice were injected with Probenicid (200 mg/kg) 30 min before administration of the tested agents to assess the role of organic acid transport in elimination (duration of action). The aim was to obtain $ED_{50}$s for all parameters scored using the Litchfield Wilcoxon (1949) test for quantal dose responses.

Results

Of the compounds tested, only four compounds, all class II, were effective when given i.p. in the M.E.S. test (Mrz 2/499, Mrz 2/502, Mrz 2/516 and Mrz 2/514 see table 16a). The associated class I compounds were inactive. All four compounds apparently had very short half lives in vivo. The PTZ test seemed to be a more sensitive model for activity of glycine$_B$ antagonists given i.p. and, indeed, the same class II compounds were active at 2–4 fold lower doses whereas class I compounds remained inactive (table 16a).

The choline salts of these same N-oxide derivatives (structures II) had clear anticonvulsive activity in all three models, while their non-N-oxide derivatives were either inactive, or weak (Table 16b). Moreover it seems that choline salts have a longer duration of action. Probenecid injection prolonged considerably the duration of anticonvulsive action of all agents tested. For example the half lives of 2/514 and 2/570 were around 40 and 80 minutes respectively in the absence of probenicid. In the presence of probenicid the half lives were prolonged to around 180 and 210 minutes respectively. Thus, it seems that organic acids transport in the choroid plexus out of the brain plays an important role in the short duration of action of the compounds tested.. Probenecid at the dose used (200 mg/kg) has no independent effect on MES-induced convulsions per se.

TABLE 16a

| Mrz 2/ | Substance | MES i.p. ($ID_{50}$ mg/kg) | NMDA i.p. ($ID_{50}$ mg/kg) | PTZ i.p. ($ID_{50}$ mg/kg) |
|---|---|---|---|---|
| 585 | I | >100.0 | 58.9 | 59.0 |
| 499 | II | 87.0 | | 18.6 |
| 501 | 8-Cl-I | >100.0 | >100.0 | >40.0 |
| 502 | 8-Cl-II | 47.6 | 26.0 | 8.3 |
| 503 | 8-Br-I | >100.0 | >100.0 | >100.0 |
| 514 | 8-Br-II | 20.2 | 99.0 | 12.8 |
| 519 | 8-F-I | >60.0 | >100.0 | >100.0 |
| 516 | 8-F-II | 16.6 | 40.0 | 7.9 |
| 515 | 7,8-DiCl-I | >100.0 | 98.0 | >100.0 |
| 518 | 7,8-DiCl-II | >60.0 | >100.0 | |
| 539 | 7-Cl,8-Br-I | >60.0 | >100.0 | >100.0 |
| 538 | 7-Br,8-Cl-I | >60.0 | 106.0 | >100.0 |
| 554 | 8-O-CH$_3$-I | >100.0 | | |

TABLE 16b

| Mrz 2/ | Substance | MES i.p. ($ID_{50}$ mg/kg) |
|---|---|---|
| 577 | II (Chol) | 23.7 |
| 569 | 8-Cl-I (Chol) | >50 |
| 576 | 8-Cl-II (Chol) | 7.7 |
| 586 | 8-Br-I (Chol) | >50 |
| 570 | 8-Br-II (Chol) | 12.8 |
| 572 | 8-F-I (Chol) | >100 |
| 571 | 8-F-II (Chol) | 15.5 |
| 574 | 7,8-DiCl-I (Chol) | >100 |
| 578 | 8-O-CH$_3$-II (Chol) | >100.0 |
| 575 | 7-O-CH$_3$-I (Chol) | >100.0 |

Microelectrophoretic application of EAA agonists to spinal neurones in vivo

The ability of these glycine$_B$ antagonists to act as NMDA receptor antagonists in vivo was assessed using i.v. administration against responses of single neurones in the rat spinal cord to microelectrophoretic application of AMPA and NMDA. The class II compounds Mrz 2/502 and Mrz 2/516 were potent NMDA receptor antagonists in vivo with $ID_{50}$s of 1.2 and 1.8 mg/kg i.v. respectively whereas the parent class I compounds were completely inactive at up to 16 mg/kg i.v. Three to four fold higher doses also antagonised responses to AMPA, although this apparent lack of selectivity contrasts with the in vitro assays (Table 17a).

TABLE 17a

| Mrz 2/ | Substance | Microelectrophoretic NMDA ($ID_{50}$ mg/kg i.v.) | Microelectrophoretic AMPA ($ID_{50}$ mg/kg i.v.) |
|---|---|---|---|
| 501 | 8-Cl-I | >16.0 | >16.0 |
| 502 | 8-Cl-II | 1.2 | 4.9 |
| 519 | 8-F-I | >16.0 | >16.0 |
| 516 | 8-F-II | 1.8 | 3.6 |

The choline salts were about equipotent as the free acids in this model following i.v. administration but were somewhat more selective for NMDA versus AMPA (Table 17b). Once again, the non-N-oxide derivatives (class I compounds) were inactive.

TABLE 17b

| Mrz 2/ | Substance | Microelectrophoretic NMDA ($ID_{50}$ mg/kg i.v.) | Microelectrophoretic AMPA ($ID_{50}$ mg/kg i.v.) |
|---|---|---|---|
| 577 | II (Chol) | 34.0 | >32.0 |
| 569 | 8-Cl-I (Chol) | >16.0 | >16.0 |
| 576 | 8-Cl-II (Chol) | 2.8 | >16.0 |
| 586 | 8-Br-I (Chol) | >16.0 | >16.0 |
| 570 | 8-Br-II (Chol) | 4.5 | >16.0 |
| 572 | 8-F-I (Chol) | >16.0 | >16.0 |
| 571 | 8-F-II (Chol) | 4.7 | 9.2 |

DISCUSSION

The four class II compounds Mrz 2/499, 2/501, 2/514 and 2/516 are glycine$_B$ antagonists in vitro and have a much better in vivo systemic and / or CNS availability than their associated parent class I compounds (Mrz 2/585, 2/501, 2/503 and 2/519). Access to the CNS is a major problem for almost all glycine$_B$ antagonists developed to date, but this new class of compounds has overcome this major hindrance and are accordingly therapeutically relevant glycine$_B$ antagonists.

ADDITION SALTS

By using methods as outlined hereinbefore for compounds 5, 6, 7, 8, 9, and 10, addition salts are prepared with quaternary amines (e.g., 4-tetramethylammonium, 4-tetraethylammonium), quaternary aminoalcohols (e.g., choline), or quaternary aminoacids (e.g., N,N,N-trimethylserine). Choline and 4-tetramethylammonium (4-NH₃) salts improve bioavailability substantially and are preferred.

PHARMACEUTICAL COMPOSITIONS

The compounds according to the present invention may be processed into pharmaceutical compositions comprising a pharmaceutically-acceptable carrier or diluent in addition to the active compound of the present invention. Such compositions can be administered to a living animal, especially a living human, by the oral or the parenteral route. For example, solid preparations or pharmaceutical compositions for oral administration may take the form of capsules, tablets, pills, powders, or granulates. In such solid pharmaceutical formulations, the active substance or a prodrug therefor is mixed with at least one pharmaceutically-acceptable diluent or carrier such as cane sugar, lactose, starch, talc, or synthetic or natural gums, a binder such as gelatin, a lubricant such as sodium stearate, and/or a disintegrant such as sodium bicarbonate. To enable a sustained-release effect, a substance such as a hydrocolloid or other polymer may be incorporated into the pharmaceutical composition. Additional substances such as lubricants or buffers may also be added, as is conventional in the art. The tablets, pills, or granulates may be subjected to enteric coating, if desired. Liquids for oral application may be in the form of liposomes, emulsions, solutions, or suspensions, containing commonly-used inert diluents such as water. Additionally, such liquid pharmaceutical compositions may also contain wetting, emulsifying, dispersing, or generally surface-active agents as well as sweetening, flavoring, or fragrance-imparting substances.

Suitable preparations for parenteral application may be, among others, sterile aqueous or non-aqueous solutions, suspensions, liposomes, or emulsions. Additional substances, of which there are many, already known for this form of presentation of a pharmaceutical composition, may be employed as pharmaceutically-acceptable diluent or carrier material.

Depending upon the intended mode of application and duration of treatment, the exact dosage of the active compounds in the preparations of the invention may be varied, especially as deemed appropriate by the attending physician or veterinarian. The active agents of the present invention may obviously be combined for administration with other pharmacologically-active agents.

In the compositions of the present invention, the proportions of the active agent or agents in the composition may be varied widely, it being necessary only that the active ingredient of the invention or a prodrug therefor constitute or provide an effective amount, i.e., such that a suitable effective dose will be obtained consistent with the dosage form employed. Obviously several dosage forms as well as several individual active compounds may be administered at or about the same time or even in the same pharmaceutical composition or formulation.

METHOD-OF-TREATING

As previously indicated, the compounds of the present invention are suitable, especially in the form of pharmaceutical compositions or formulations thereof, for oral or parenteral administration, the exact individual dosages as well as daily dosages in a particular case of course being determined according to well-established medical and/or veterinarian principles in accord with the directions of the physician or veterinarian in charge.

In addition to oral and parenteral administration, rectal and/or intravenous administration may be employed, the dosages generally being considerably reduced where parenteral administration is involved, although oral administration is preferred. An amount of approximately one to three grams per day in the form of repeated or divided dosages is suitable. Broader ranges of about 0.5 to about 10 grams per day may also be employed, depending upon the circumstances of an individual case. Although 500 mg of active principle has been found especially suitable for use in tablets, individual dosages may vary from about 200 to 1,000 mg, and the 500 mg suggested for use in tablets may of course be administered orally, for example, from one to three times a day. It goes without saying that more than one tablet may be administered in a single dose, as would be required to attain the above-identified suggested daily oral administration amounts of one to three grams per day.

As already stated, a compound of the invention or a prodrug therefor may be administered to the living animal including a living human in any one of numerous ways, for example, orally as in capsules or tablets, parenterally in the form of sterile solutions or suspensions, or by pellet implantation, and in some cases intravenously in the form of sterile solutions. Other obvious modes of administration are cutaneously, subcutaneously, bucally, intramuscularly, and intraperitoneally, and the particular mode of administration will as usual be selected by the physician or veterinarian in charge.

It is thus seen that the present invention provides novel pyrido-phtalazin dione compounds and pharmaceutical compositions thereof, as well as a method of combating neurological disorders associated with excitotoxicity and malfunctioning of glutamatergic neurotransmission therewith, these collectively providing a long-awaited solution to a previously-existing problem not adequately solved by the prior art.

It is to be understood that the present invention is not to be limited to the exact compounds, compositions, methods, or procedures disclosed, as numerous modifications and changes therein will immediately become apparent to one skilled in the art to which this invention pertains, wherefore the present invention is to be understood as limited only by the full scope which can be legally accorded to the appended claims.

We claim:

1. A compound selected from those pyridyl-phtalazin diones having the following formula:

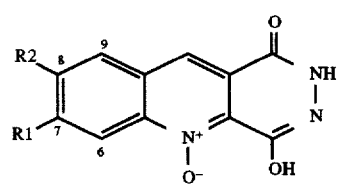

wherein R1 and R2 are selected from the group consisting of hydrogen, halogen, and methoxy or wherein R1 and R2 together form methylenedioxy, or a pharmaceutically-acceptable salt thereof.

2. A compound of claim 1 wherein the salt is selected from a choline and a 4-tetramethyl ammonium salt thereof.

3. A compound of claim 1 which is selected from the group consisting of 4-hydroxy-1-oxo-1,2-dihydro-pyridazino[4,5-b]-quinoline 5-oxide, 8-chloro-4-hydroxy-1-oxo-1,2-dihydropyridazino[4,5-b]-quinoline 5-oxide, 8-bromo-4-hydroxy-1-oxo-1,2-dihydropyridazino(4,5-b)-quinoline 5-oxide, 8-fluoro-4-hydroxy-1-oxo-1,2-dihydropyridazino[4,5-b]-quinoline 5-oxide, 7,8-dichloro-4-hydroxy-1-oxo-1,2-dihydropyridazino-[4,5-b]-quinoline 5-oxide, 7-bromo-8-chloro-4-hydroxy-1-oxo-1,2-dihydropyridazino-[4,5-b]-quinoline 5-oxide, and 7-chloro-8-bromo-4-hydroxy-1-oxo-1,2-dihydropyridazino-[4,5-b]-quinoline 5-oxide, and a pharmaceutically-acceptable salt of any of the foregoing.

4. A compound of claim 2 selected from the group consisting of 4-hydroxy-1-oxo-1,2-dihydro-pyridazino[4,5-b]-quinoline 5-oxide choline salt, 8-chloro-4-hydroxy-1-oxo-1,2-dihydropyridazino[4,5-b]-quinoline 5-oxide choline salt, 8-bromo-4-hydroxy-1-oxo-1,2-dihydropyridazino[4,5-b]-quinoline 5-oxide choline salt, 8-fluoro-4-hydroxy-1-oxo-1,2-dihydropyridazino[4,5-b]-quinoline 5-oxide choline salt, 7,8-dichloro-4-hydroxy-1-oxo-1,2-dihydropyridazino-[4,5-b]-quinoline 5-oxide choline salt, 7-bromo-8-chloro-4-hydroxy-1-oxo-1,2-dihydropyridazino-[4,5-b]-quinoline 5-oxide choline salt, and 7-chloro-8-bromo-4-hydroxy-1-oxo-1,2-dihydropyridazino-[4,5-b]-quinoline 5-oxide choline salt.

5. A pharmaceutical composition containing as active ingredient an effective glycine$_B$ antagonistic amount of a compound of claim 1 together with a pharmaceutically-acceptable carrier or diluent.

6. A pharmaceutical composition containing as active ingredient an effective glycine$_B$ antagonistic amount of a compound of Claim 1 in the form of a choline salt thereof together with a pharmaceutically-acceptable carrier or diluent.

7. A pharmaceutical composition containing as active ingredient an effective glycine$_B$ antagonistic amount of a compound selected from the group consisting of 4-hydroxy-1-oxo-1,2-dihydro-pyridazino[4,5-b]-quinoline 5-oxide, 8-chloro-4-hydroxy-1-oxo-1,2-dihydropyridazino[4,5-b]-quinoline 5-oxide, 8-bromo-4-hydroxy-1-oxo-1,2-dihydropyridazino[4,5-b]-quinoline 5-oxide, 8-fluoro-4-hydroxy-1-oxo-1,2-dihydropyridazino[4,5-b]-quinoline 5-oxide, 7,8-dichloro-4-hydroxy-1-oxo-1,2-dihydropyridazino-[4,5-b]-quinoline 5-oxide, 7-bromo-8-chloro-4-hydroxy-1-oxo-1,2-dihydropyridazino-[4,5-b]-quinoline 5-oxide, and 7-chloro-8-bromo-4-hydroxy-1-oxo-1,2-dihydropyridazino-[4,5-b]-quinoline 5-oxide, or a pharmaceutically-acceptable salt of any of the foregoing.

8. A pharmaceutical composition containing as active ingredient an effective glycine$_B$ antagonistic amount of a compound selected from the group consisting of 4-hydroxy-1-oxo-1,2-dihydro-pyridazino[4,5-b]-quinoline 5-oxide choline salt;

8-chloro-4-hydroxy-1-oxo-1,2-dihydropyridazino[4,5-b]-quinoline 5-oxide choline salt, 8-bromo-4-hydroxy-1-oxo-1,2-dihydropyridazino[4,5-b]-quinoline 5-oxide choline salt, 8-fluoro-4-hydroxy-1-oxo-1,2-dihydropyridazino[4,5-b]-quinoline 5-oxide choline salt, 7,8-dichloro-4-hydroxy-1-oxo-1,2-dihydropyridazino-[4,5-b]-quinoline 5-oxide choline salt, 7-bromo-8-chloro-4-hydroxy-1-oxo-1,2-dihydropyridazino-[4,5-b]-quinoline 5-oxide choline salt, and 7-chloro-8-bromo-4-hydroxy-1-oxo-1,2-dihydropyridazino-[4,5-b]-quinoline 5-oxide choline salt.

9. A method of combatting a neurological disorder, selected from epilepsy, ischemia, anxiety, opioid dependence, and pain, in a living animal comprising the step of administering to a living animal in need thereof an effective glycine antagonistic amount of a compound of claim 1.

10. A method of combatting a neurological disorder, selected from epilepsy, ischemia, anxiety, opioid dependence, and pain, in a living animal comprising the step of administering to a living animal in need thereof an effective glycine$_B$ antagonistic amount of a compound of claim 1 in the form of a choline salt thereof.

11. A method of combatting a neurological disorder selected from epilepsy, ischemia, anxiety, opioid dependence, and pain, in a living animal comprising the step of administering to a living animal in need thereof an effective glycine$_B$ antagonistic amount of a compound selected from the group consisting of 4-hydroxy-1-oxo-1,2-dihydro-pyridazino[4,5-b]-quinoline 5-oxide, 8-chloro-4-hydroxy-1-oxo-1,2-dihydropyridazino[4,5-b]-quinoline 5-oxide, 8-bromo-4-hydroxy-1-oxo-1,2-dihydropyridazino[4,5-b]-quinoline 5-oxide, 8-fluoro-4-hydroxy-1-oxo-1,2-dihydropyridazino[4,5-b]-quinoline 5-oxide, 7,8-dichloro-4-hydroxy-1-oxo-1,2-dihydropyridazino-[4,5-b]-quinoline 5-oxide, 7-bromo-8-chloro-4-hydroxy-1-oxo-1,2-dihydropyridazino-[4,5-b]-quinoline 5-oxide, and 7-chloro-8-bromo-4-hydroxy-1-oxo-1,2-dihydropyridazino-[4,5-b]-quinoline 5-oxide, or a pharmaceutically-acceptable salt of any of the foregoing.

12. A method of combatting a neurological disorder, selected from epilepsy, ischemia, anxiety, opioid dependence, and pain, in a living animal comprising the step of administering to a living animal in need thereof an effective glycine$_B$ antagonistic amount of a compound selected from the group consisting of 4-hydroxy-1-oxo-1,2-dihydro-pyridazino[4,5-b]-quinoline 5-oxide choline salt, 8-chloro-4-hydroxy-1-oxo-1,2-dihydropyridazino[4,5-b]-quinoline 5-oxide choline salt, 8-bromo-4-hydroxy-1-oxo-1,2-dihydropyridazino[4,5-b]-quinoline 5-oxide choline salt, 8-fluoro-4-hydroxy-1-oxo-1,2-dihydropyridazino[4,5-b]-quinoline 5-oxide choline salt, 7,8-dichloro-4-hydroxy-1-oxo-1,2-dihydropyridazino-[4,5-b]-quinoline salt, 7-bromo-8-chloro-4-hydroxy-1-oxo-1,2-dihydropyridazino-[4,5-b]-quinoline 5-oxide choline 5-oxide choline salt, and 7-chloro-8-bromo-4-hydroxy-1-oxo-1,2-dihydropyridazino-[4,5-]-quinoline 5-oxide choline salt.

* * * * *

UNITED STATES PATENT AND TRADEMARK OFFICE
CERTIFICATE OF CORRECTION

PATENT NO. : 5,776,935

DATED : July 7, 1998

INVENTOR(S) : Wojciech Danysz, Markus Gold, Ivars Kalvinsh, Christopher Graham Raphael Parsons, Irene Piskunova, & Eugene Rozhkov It is certified that error appears in the above-indentified patent and that said Letters Patent is hereby corrected as shown below:

Page 1, third reference in Col. 1: "screenig" should be --screening--

Col. 2, last reference, line 2: "287" should be --28--

Col. 1, last reference, line 4: "in" should be --of--

Col. 2, fourth paragraph, line 3: "learning rats" should be --learning in rats--

Col. 9, line 59: Insert --1H)-- after "2.0,"

Col. 18, line 35: "cm" should be --$cm^{-2}$--
line 11 after Table 13b.
Claim 9, Col. 26, line 25: "glycine" should be --$glycine_B$--

Claim 12, Col. 27, line 4: "quinoline salt" should be --quinoline 5-oxide choline salt-- and "7-bromo-8-chloro-4-hydroxy-1-" should be moved down one line Claim 12, Col. 28, line 2: "4,5" should be --4,5-b--

Signed and Sealed this

Ninth Day of February, 1999

Attest:

*Attesting Officer*

*Acting Commissioner of Patents and Trademarks*